(12) United States Patent
Pineau et al.

(10) Patent No.: US 7,918,794 B2
(45) Date of Patent: Apr. 5, 2011

(54) METHOD AND SYSTEM FOR DETERMINING TOTAL BODY FAT, AND METHOD AND SYSTEM FOR DETERMINING BODY COMPOSITION

(75) Inventors: Jean-Claude Pineau, Paris (FR); Michel Bocquet, Cergy Saint-Christophe (FR); Eric Crescenzo, Gergy (FR)

(73) Assignee: Centre National de la Recherche Scientifique, Paris (FR)

( * ) Notice: Subject to any disclaimer, the term of this patent is extended or adjusted under 35 U.S.C. 154(b) by 713 days.

(21) Appl. No.: 11/379,493

(22) Filed: Apr. 20, 2006

(65) Prior Publication Data
US 2007/0038092 A1 Feb. 15, 2007

(51) Int. Cl.
*A61B 8/00* (2006.01)
(52) U.S. Cl. ........ 600/438; 600/547; 600/442; 600/554; 600/449
(58) Field of Classification Search .................. 600/438, 600/547
See application file for complete search history.

(56) References Cited

U.S. PATENT DOCUMENTS
5,335,667 A * 8/1994 Cha et al. ...................... 600/547
5,941,825 A * 8/1999 Lang et al. ..................... 600/449

FOREIGN PATENT DOCUMENTS
EP   1055396 A2 * 11/2000

OTHER PUBLICATIONS

Friedl et al. "Evaluation of anthropometric equations to assess body-composition changes in young women." American Journal of Clinical Nutrition, vol. 73, No. 2, 268-275, Feb. 2001.*

* cited by examiner

*Primary Examiner* — Long Le
*Assistant Examiner* — Nigel Fontenot
(74) *Attorney, Agent, or Firm* — Holland & Knight LLP; Brian J. Colandreo, Esq.; J. Mitchell Herbert, Jr., Esq.

(57) ABSTRACT

A method of determining the total body fat of a person comprising measuring a subcutaneous fat thickness at four points on the person's body, located in the right anterior part of the left mid-thigh, in the left anterior part of the right mid-thigh, in the right dorsal part navel level and in the left dorsal part at navel level, respectively, and determining a first estimate of the person's total body fat as a function of these measurements.

11 Claims, 3 Drawing Sheets

METHOD AND SYSTEM FOR DETERMINING TOTAL BODY FAT, AND METHOD AND SYSTEM FOR DETERMINING BODY COMPOSITION

RELATED APPLICATIONS

The subject application is a U.S. National Stage application that claims the priority of International Application No. PCT/FR2004/002625, filed on 14 Oct. 2004, which claims the priority of French National Application No. 03 12234 filed on 20 Oct. 2003.

FIELD OF INVENTION

The present invention relates to the field of techniques for determining a human's total body fat. A person's total mass is split between, on the one hand, the lean body mass, made up of muscles, mineral content and total water, and, on the other hand, the fat. A person's body composition is defined by the values of the body fat, the lean body mass and the total (intracellular and extracellular) body water present in his body. Under certain conditions, composition may be determined from the body fat.

BACKGROUND OF THE INVENTION

Many disciplines use the total body fat values or body composition values of individuals. These disciplines may for example include epidemiology, where the aim is to find the various factors relating to body composition and fat values of a specimen representative of groups of individuals and determine the occurrence, frequency, method of spread and evolution of diseases affecting these groups of individuals.

Moreover, these concepts of body fat or composition may also be used within the context of establishing or monitoring specific diets, or body remodeling, for the general public (services available over the Internet or in beauty parlors) or for paramedical or medical personnel. Teams of practitioners are in particular specializing in the monitoring of high-level sportsmen.

There are several techniques for determining a person's total body fat. Some of these techniques are analyzed in the document by H. C. Lukaski "Methods for the assessment of human body composition: traditional and new" (Amer. J. Clin. Nutr. 1987, 46, 537-56). The measurement obtained by dual-photon absorptiometry, also called DEXA (Dual Energy X-ray Absorptiometry) provides very reliable results and is a reference method for total body fat and for body composition. It consists in irradiating the person with a beam of photons having two different energies, and it makes it possible to distinguish absorption by the various tissues and to calculate their mass. However, it has the drawback of requiring the person being measured to be irradiated with a low dose of X-rays and of being able to be carried out only in hospital.

Moreover, medical resonance imaging or MRI allows the body fat to be determined in as many of the person's sections as planes of sections made during the examination. It is then possible from these measurements in the planes of section to estimate the total body fat. This technique is described for example in the document by T. S. Han, I. E. Kelly, K. Walsh, R. M. E. Greene and M. E. J. Lean, "Relationship between volumes and areas from single transverse scans of intra abdominal fat measured by magnetic resonance imaging" (Int. J. Obes. 1997, 21, 1161-1166). However, the procedure is lengthy and the equipment required is expensive. This technique, which can only be carried out in a hospital, is not suitable for routine examinations owing to the extent of the means employed.

There are also techniques that can be implemented away from hospitals and require less expensive equipment than the DEXA or MRI methods. Among these, mention may be made of the skinfold caliper method, which consists in firmly taking hold of a fold of skin and in determining, from the thickness of the fold and from mathematical equations, the body fat. However, this determination technique is subject to errors during measurement by the operators. Furthermore, in particular it is not valid for the obese.

Moreover, document U.S. Pat. No. 5,941,825 ("Measurement of body fat using ultrasound methods and devices" by Stephan Gramp, Philipp Lang and John Mendlein) describes a technique for determining a person's total body fat using the same principle as that presented by Jackson and Pollock in 1978 using the skinfold caliper method, who determined by using a formula, the percentage total fat by means of fat thickness measurements taken in the arms, chest, abdomen, back and thighs. Document U.S. Pat. No. 5,941,825 employs a novel formula and a fat thickness measurement principle based on ultrasound.

According to document U.S. Pat. No. 5,941,825, the local subcutaneous fat thickness is measured using an ultrasound device at 11 points. These points correspond to the following respective regions: medial calf; lateral calf; anterior thigh; posterior thigh; triceps; biceps; chest; abdomen; axilla; sub-scapular region; and suprailiac region. A fat volume is then deduced on the basis of these eleven local fat thickness values using a formula, and this estimated volume is multiplied by a fat density in order to determine the total body fat.

This technique has the advantage of being able to be carried out in nonmedical establishments. However, it does require a relatively lengthy measurement step, since it involves eleven points. Moreover, a comparative study of the results provided by this method and those provided by the DEXA reference technique highlights appreciable differences.

SUMMARY OF THE INVENTION

It is an object of the present invention to alleviate at least some of the limitations of the body fat determination techniques of the prior art.

Thus, the first subject of the present invention is a method of determining the total body fat of a person, characterized in that it comprises the following steps:

a subcutaneous fat thickness is measured at four points on the person's body, located in the right anterior part of the left mid-thigh, in the left anterior part of the right mid-thigh, in the right dorsal part at navel level and in the left dorsal part at navel level, respectively; and a first estimate of the person's total body fat is then determined as a function of at least the subcutaneous fat thickness measurements at said four points.

The method according to the invention thus makes it possible to estimate the total body fat from the subcutaneous fat thickness measurements taken at a fewer number of points—the determination can therefore be implemented rapidly.

Advantageously, the local subcutaneous fat thickness measurements may be carried out using an ultrasound device. Thus, the method may be carried out in any building and does not require a medical environment. In addition, it prevents the traumatism generated by any exposure to X-rays, even of very short duration.

However, in another method of implementation, allowing more rapid determination of the total body fat, the subcutaneous fat thickness at at least some of these points may be measured using other means (skinfold caliper, etc.). It may also be estimated—and not measured—for example using charts and anthropometric data relating to the individual, such as his weight and height and the perimeter of certain sections of his body, which are provided by commonplace devices (scales, measuring tape). However the accuracy of the result obtained would be less.

In preferred ways of implementing the method according to the invention, one or other of the following arrangements may be employed:

the first estimate of the person's total body fat is also a function of values representative of the perimeter around the waist passing through the navel, the perimeter around the leg passing through mid-thigh, the body mass index, defined as the ratio of a person's weight to the square of his height, and the sex of the person;

the first estimate of the person's total body fat is a linear function of the subcutaneous fat thickness measurements at said four points;

the first estimate of the person's total body fat is obtained using the equation below:

$$FAT = a \times BMI + b \times T_{nav,l} + c \times T_{nav,r} + d \times WP + e \times T_{thigh,r} + f \times T_{thigh,l} + g \times AP_{thigh} + constant,$$

where FAT is the first estimate of the total body fat in kg, BMI is the ratio of the person's weight in kg to the square of his height in m, WP is the waist perimeter passing through the navel, $AP_{thigh}$ is the average of the left and right leg perimeters passing at mid-thigh, $T_{nav,l}$, $T_{nav,r}$, $T_{thigh,r}$ and $T_{thigh,l}$ are the fat thicknesses measured in the left dorsal part at navel level, in the right dorsal part at navel level, in the right anterior part of the left mid-thigh and in the left anterior part of the right mid-thigh, in mm, respectively, and where a=0.959, b=0.119, c=−0.044, d=0.13, e=0.586, f=−0.329, g=0.061 and constant=−23.88, when the person is of the female sex; and a=0.733, b=−0.053, c=0.102, d=0.27, e=0.155, f=−0.106, g=0.015 and constant=−31.21 when the person is of the male sex;

the method further includes a step in which the first estimate of the person's total body fat is compared with a threshold defined by sex followed by a step of determining a second estimate of the person's total body fat as a function of the results of the comparison and of at least the subcutaneous fat thickness measurements at said four points;

the second estimate of the person's total body fat is also a function of at least values representative of the perimeter around the waist passing through the navel, the perimeter around the leg passing through mid-thigh, the body mass index, defined as the ratio of the person's weight to the square of his height, and the sex of the person;

the second estimate of the person's total body fat is obtained using a linear function of the cutaneous thickness measurements at said four points; and the second estimate of the person's total body fat is obtained using the equation below:

$$FAT = a - BMI + b \times T_{nav,l} + c \times T_{nav,r} + d \times WP + e \times T_{thigh,r} + f \times T_{thigh,l} + g \times AP_{thigh} + constant, \text{ when the person is of the female sex,}$$

where a=0.947, b=0.079, c=0.0067, d=0.103, e=−0.303, f=0.379, g=0.072 and constant=−20.58 if the first estimate is below the predefined threshold of 42 kg, and a=−0.743, b=−1.73, c=1.10, d=1.677, e=−3.35, f=2.62, g=−4.95 and constant=242.53 if the first estimate is equal to or greater than the predefined threshold of 42 kg, and using the following equation when the person is of the male sex:

$$FAT = a \times BMI + b \times T_{nav,l} + c \times T_{nav,r} + d \times WP + e \times T_{thigh,r} + f \times T_{thigh,l} + g \times AP_{thigh} + h \times T_{thigh,av} + i \times T_{nav,av} + constant$$

where $T_{thigh,av}$ is the average fat thickness at mid-thigh and $T_{nav,av}$ is the average dorsal fat thickness at navel level, and where a=0.221, b=0.032, c=0.06, d=0.253, e=0.078, f=−0.0128, g=0.073, h=−0.048, i=−0.028 and constant=−21.2 if the first estimate is below the predefined threshold of 22 kg and a=1.31, b=−2.69, c=−1.76, d=−0.175, e=10.33, f=8.91, g=−0.123, h=−18.97, i=4.72 and constant=−10.88 if the first estimate is equal to or greater than the predefined threshold of 22 kg.

A second subject of the invention is a method of determining a person's body composition, in which the steps of a method for determining the person's total body fat as defined above are carried out and then, from the body fat determined, a value of the lean body mass and a value of the total body water present in the person's body are determined.

Advantageously, the value of the lean body mass is equal to the person's weight from which a determined fat value is subtracted and the total body water value is equal to:

$$W_{body} = 0.692 \times LBM + 1.572, \text{ where } W_{body} \text{ is the total body water (in liters) and LBM is the lean body mass (in kilograms).}$$

A third and fourth subject of the invention are, respectively, a system for determining a person's total body fat and a system for determining a person's body composition, comprising means for implementing the steps of a method according to the first subject and according to the second subject of the invention, respectively.

Such systems according to the invention are reliable systems for determining the total body fat and the total body composition, respectively, which can be easily transported from one site to another and can be used in applications not requiring medical personnel. This feature is beneficial in particular in the monitoring of sportsmen, as it allows a routine check of the total body fat to be readily made when going from one sporting event to another.

BRIEF DESCRIPTION OF THE DRAWINGS

Other features and advantages of the invention will become more apparent on reading the description that follows, which is purely illustrative and must be read in conjunction with the appended drawings in which.

DESCRIPTION OF PREFERRED EMBODIMENTS

Figure 1:
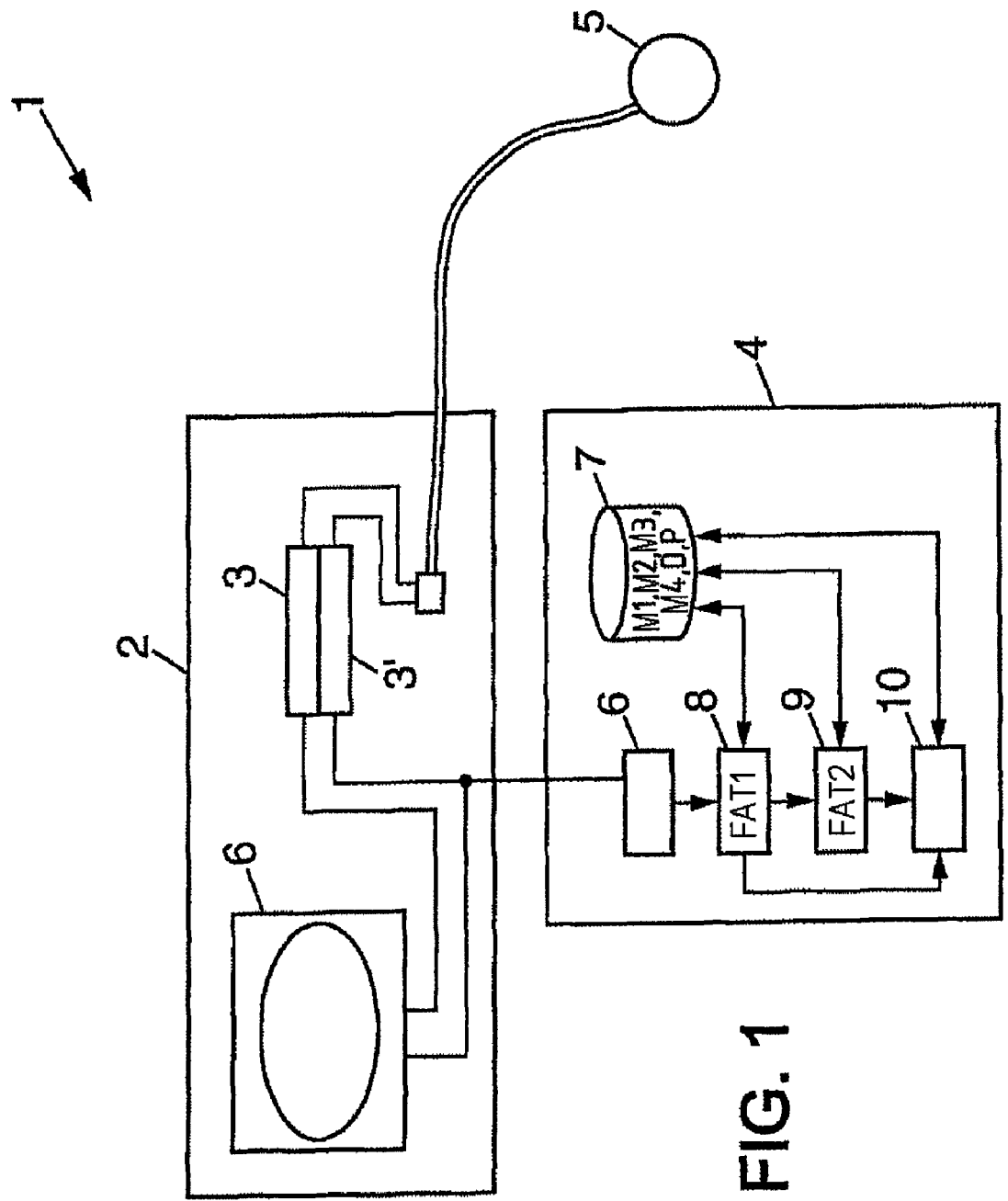
FIG. 1 is a diagram showing the principle of one embodiment of a system according to the invention.

FIG. 1 is a diagram showing the principle of one embodiment of a system 1 according to the invention. This system includes an echograph 2. This echograph 2 is for example an A-scan or uniaxial echograph.

The echograph 2 includes a drive circuit 3 and a receive circuit 3' which, respectively, generate ultrasound firings from an ultrasonic transceiver probe 5 and collect the echoes received by the probe 5 following these firings. The probe 5 connected to the circuits 3 and 3' is for example a single-element or two-element, focusing or nonfocusing, straight probe used in particular in veterinary applications for measuring fat thickness in pigs.

The device further includes, in one advantageous embodiment, a computer 4 connected to the echograph 2. This computer 4 has a subcutaneous fat thickness determination module 6 suitable for controlling the drive circuit 3 and for processing the echo measurements delivered in succession by the receive circuit 3', so as to extract therefrom representative values of a local subcutaneous fat thickness corresponding to the position of the probe 5, for example after a calibration phase for adjusting the gain and the amplitude of the echograph 2.

In another embodiment, the correspondence between the amplitude of the measured echoes and the subcutaneous fat thickness is made using charts.

The operation of a device for ultrasonically determining a subcutaneous fat thickness is well known to those skilled in the art (see for example document WO 99/65395).

The system 1 advantageously includes a memory 7 for storing the computed body fat thicknesses. This storage may take place automatically or upon validation of the operator of the system 1.

In the embodiment shown in FIG. 1, the computer 4 also includes a first total body fat determination module 8 that calculates a first total body fat estimate FAT1 of a person, by calculating a linear function F from a set of four subcutaneous fat thickness measurements $M_{nav,l}$, $M_{nav,r}$, $M_{thigh,r}$ and $M_{thigh,l}$ stored in the memory 7 and from other data D that may be input by the operator before the calculation, or are themselves stored beforehand in the memory 7.

The computer 4 includes a second total body fat determination module 9 which firstly makes a comparison between the first estimate FAT1 delivered by the module 8 and a predetermined threshold that depends on the sex of the person, $PT_w$, being the predetermined threshold for women ($PT_w$=42 kg) and $PT_m$ being the predetermined threshold for men ($PT_m$=22 kg) then calculating a second estimate FAT2 of a person's total body fat by means of a linear function that depends on the results of the comparison, using the four subcutaneous fat thickness measurements $M_{nav,l}$, $M_{nav,r}$, $M_{thigh,r}$ and $M_{thigh,l}$ stored in the memory 7 and the data D.

The computer 4 includes a third module 10 for determining the total body composition, which, on the basis of the total body fat estimate FAT2 determined by the module 9 (or based on the total body fat estimate FAT1 determined by the module 8), delivers an estimate of the lean body mass and the total water present in the person's body.

The echograph 2 also includes a screen 6 for displaying the measurements made.

The operating mode for determining a person's total body fat is the following: after having applied a coupling gel between the probe 5 and the person's skin, an operator takes a subcutaneous fat thickness measurement at four points, $M_{nav,l}$, $M_{nav,r}$, $M_{thigh,r}$ and $M_{thigh,l}$, on the person's body by applying the probe 5 in succession at each of these points and by firing an ultrasound pulse via the circuit 3 of the echograph 2. The echoes received by the probe 5 at each of these points are processed by the circuit 3' and then by the computer 6, which delivers the subcutaneous fat thickness $T_{nav,l}$, $T_{nav,r}$, $T_{thigh,r}$ and $T_{thigh,l}$ at each of the points $M_{nav,l}$, $M_{nav,r}$, $M_{thigh,r}$ and $M_{thigh,l}$. These $T_{nav,l}$, $T_{nav,r}$, $T_{thigh,r}$ values are stored in the memory 7.

Figure 2A:
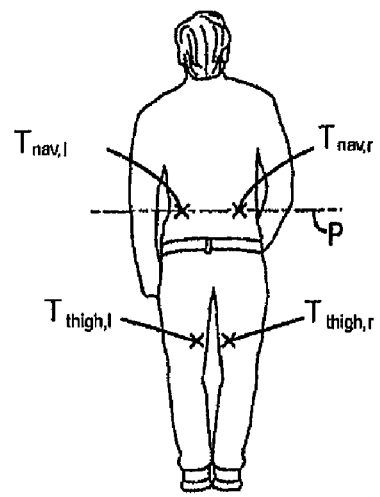
FIGS. 2a and 2b show the location of the measurement points in the embodiment of the invention illustrated in FIG. 1.

The point $M_{thigh,l}$ is located in the right anterior part of the left mid-thigh and the point $M_{thigh,r}$ is located in the left anterior part of the right mid-thigh of a person shown from behind in FIG. 2a. These points are located at about 22 cm above the knee joint, and quarter anterior, i.e. at 11.30 in the case of the right thigh and at 1.30 in the case of the left thigh, by imagining a clock for which twelve o'clock corresponds to the front extreme generatrix and 6 o'clock the rear extreme generatrix.

Figure 2B:
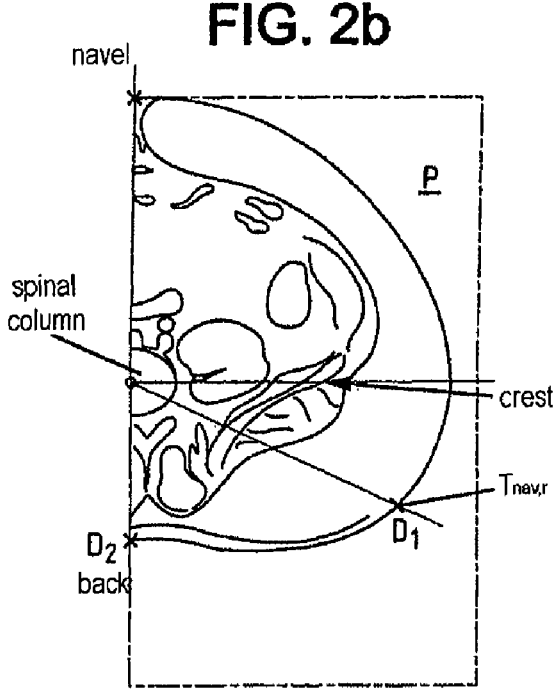

As shown on the person viewed from behind in FIG. 2a and a horizontal half-sectional view of this individual at navel level shown in FIG. 2b, the point $M_{nav,r}$ lies at right dorsal navel level, in the back, in a horizontal plane P passing through the person's trunk (in a vertical position) and passing through the navel, the straight line D1 in the plane P passing through $M_{nav,r}$ and the spinal column making an angle of about 45° to the straight line D2 in the plane P, passing through the navel and the spinal column. The point $M_{nav,l}$ is located, similarly, at left dorsal navel level. It is thus approximately symmetrical to the point $M_{nav,r}$ with respect to the straight line D2.

A set of anthropomorphic data D relating to a person is stored beforehand by the operator in memory 7. This data D comprises the sex of the person (male or female), the ratio of weight in kg to the square of the height in m (BMI), the perimeter around the waist passing through the navel (WP) and the average of the perimeters around the left and right legs passing at mid-thigh ($AP_{thigh}$)

Next, a first estimate in kg of the person's total body fat defined by the following linear equation:

$$FAT1 = a \times BMI + b \times T_{nav,l} + c \times T_{nav,r} + d \times WP + e \times T_{thigh,r} + f \times T_{thigh,l} + g \times AP_{thigh} + \text{constant}, \quad (E1)$$

with a=0.959, b=0.119, c=−0.044, d=0.13, e=0.586, f=−0.329, g=0.061 and constant=−23.88 when the individual is of the female sex, and a=0.733, b=−0.053, c=0.102, d=0.27, e=0.155, f=−0.106, g=0.015 and constant=−31.21 when the individual is of the male sex, is then calculated by means of the total body fat determination module 8.

Next, these results are refined by means of the module 9, which calculates a new estimate FAT2 of the person's body fat after having compared the first estimate obtained, i.e. FAT1, with the threshold $PT_w$ if the person is of the female sex and with the threshold $PT_m$ if the person is of the male sex, respectively.

This second estimate FAT2 is defined as follows: if the person is of the female sex, from the data D and the subcutaneous fat thickness measurements used for determining the first estimate:

$$FAT2 = a \times BMI + b \times T_{nav,l} + c \times T_{nav,r} + d \times WP + e \times T_{thigh,r} + f \times T_{thigh,l} + g \times AP_{thigh} + \text{constant},$$

where a=0.947, b=0.079, c=−0.0067, d=0.103, e=−0.303, f=0.379, g=0.072 and constant=−20.58 if the first estimate FAT1 is below a predetermined threshold $PT_w$, of 42 kg; and and a=−0.743, b=−1.73, c=1.10, d=1.677, e=−3.35, f=2.62, g=−4.95 and constant=242.53 if the first estimate FAT1 is equal to or above the predetermined threshold $PT_w$ of 42 kg;

and in the manner below, if the person is of the male sex, from the data D and the subcutaneous fat thickness measurements used for determining the first estimate:

$$FAT2 = a \times BMI + b \times T_{nav,l} + c \times T_{nav,r} + d \times WP + e \times T_{thigh,r} + f \times T_{thigh,l} + g \times AP_{thigh} + h \times T_{thigh,av} + i \times T_{umb,av} + \text{constant}$$

where $T_{thigh,av}$ is the average fat thickness at mid-thigh, i.e. half the sum of $T_{thigh,r}$ and $T_{thigh,l}$, and $T_{umb,av}$ is the average fat thickness at dorsal navel level, i.e. half the sum of $T_{nav,l}$ and $T_{nav,r}$:

and where a=0.221, b=0.032, c=0.06, d=0.253, e=0.078, f=−0.0128, g=0.073, h=−0.048, i=−0.028 and constant=−21.2 if the first estimate FAT1 is below the predetermined threshold $PT_m$ of 22 kg; and and a=1.31, b=−2.69, c=−1.76, d=−0.175, e=10.33, f=8.91, g=−0.123, h=−18.97, i=4.72 and constant=−10.88 if the first estimate FAT1 is equal to or above the predetermined threshold $PT_m$, of 22 kg.

In one embodiment of the invention, a person's body composition is calculated using the module 10. The person's weight Wt, stored beforehand in the memory 7 by the operator, is equal to the sum of lean mass and fat mass of his body. Thus, since the person's body fat has been estimated beforehand, the lean body mass LBM is obtained by subtracting the body fat mass from the person's weight, i.e. LBM=Wt−FAT2.

Next, the total body water $W_{body}$ is estimated using the following equation: $W_{body} = 0.692 LBM + 1.572$, where the total body water $W_{body}$ is expressed in liters and the lean body mass LBM in kilograms.

In a preferred embodiment, the calculated values FAT2, LBM and $W_{body}$ are recorded in memory 7. This allows the operator to be able to access a person's history and to display the change in his profile over the course of time.

Figure 3A:
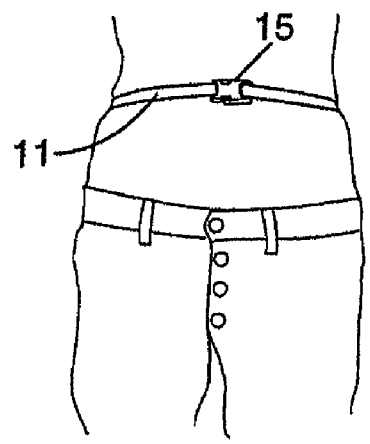
FIG. 3a shows a person seen from the front, around whom a belt in one embodiment of a system according to the invention has been placed.
Figure 3B:
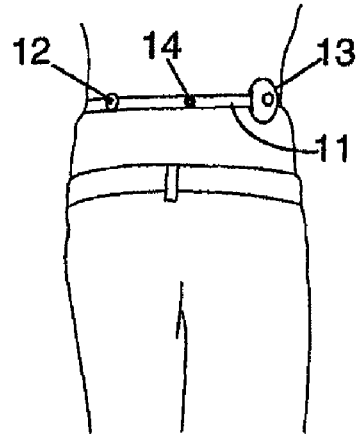
FIG. 3b shows a person seen from behind, around whom a belt in one embodiment of a system according to the invention has been placed.

In another advantageous embodiment, the operator uses a special belt 11 to be placed before the measurements are performed. This belt 11 has two dorsal lateral reference points 12, 13 on either side and at an equal distance from a central dorsal reference point 14 and a closure buckle 15, which also constitutes a central navel reference point. This belt is to be placed around the person's trunk so that the belt lies in a horizontal plane passing through the L4-L5 vertebrae and navel level. The central dorsal reference point 14 must be located on the vertical vertebral axis as shown in FIG. 3a and the central navel reference point 15 must be located on the navel.

Advantageously, two different belts may be provided. A first is for example suitable for a waist perimeter of between 50 and 90 cm and a second belt is suitable for a waist perimeter of between 80 and 150 cm.

Next, the operator can place the probe under the lateral dorsal reference points 12 and 13 and the central navel reference point 15.

Figure 4A:
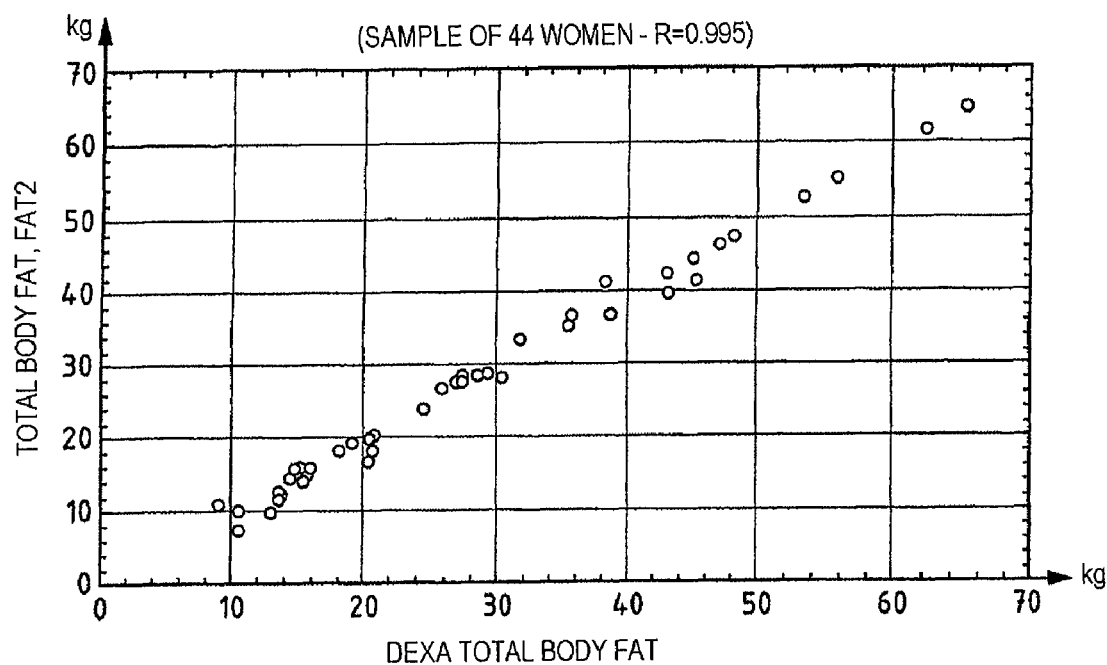
FIG. 4a illustrates the correlation, for a representative group of women, between the total body fat values determined by implementing the invention and those determined by the DEXA reference method.
Figure 4B:
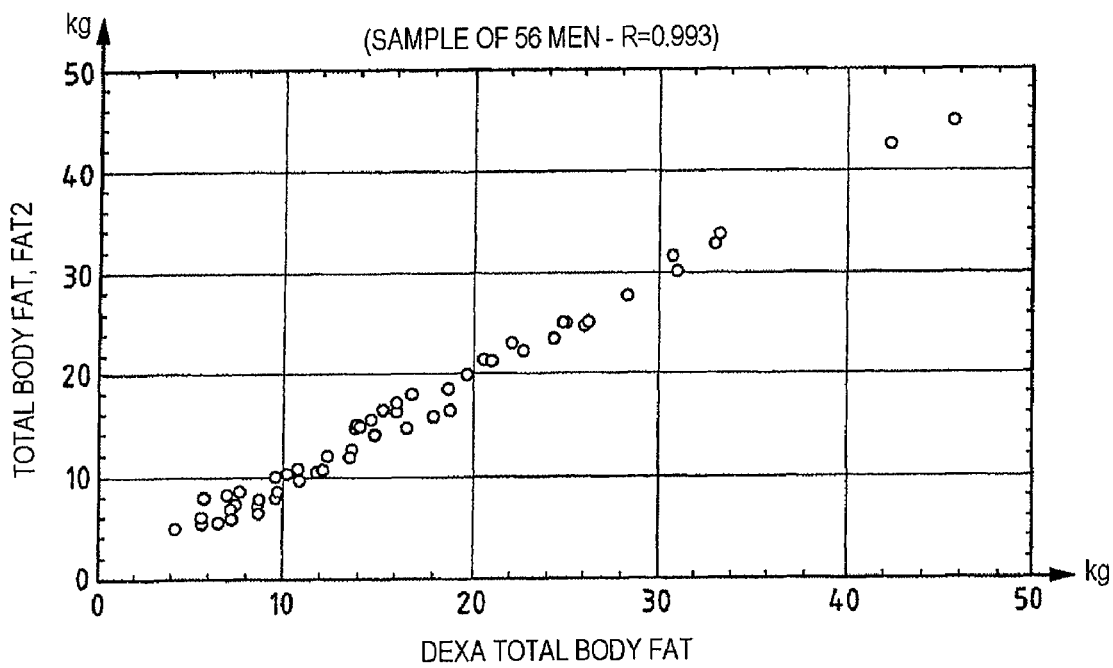
FIG. 4b illustrates the correlation, for a representative group of men, between the total body fat values determined by implementing the invention and those determined by the DEXA reference method.

According to the invention, determination of the total body fat is carried out rapidly and easily. It does not require a medical environment and it provides reliable results. FIG. 4a shows a graph in which the body fat FAT2 determined according to the invention is plotted on the x-axis and the body fat provided by the DEXA reference method is plotted on the y-axis for a sample made up of 44 women between the ages of 18 and 60 years. FIG. 4b shows a graph in which the body fat FAT2 determined according to the invention is plotted on the x-axis and the body fat provided by the DEXA reference method is plotted on the y-axis for a sample made up of 56 men aged between 18 and 60 years.

In these samples, the calculated coefficient of correlation between the second estimate FAT2 obtained according to the invention and the total body fat value provided by the DEXA reference method is R=0.995 in the case of women (corresponding to an accuracy of around 5%) and R=0.993 for men (i.e. an accuracy of around 7%).

The embodiment of the invention shown above provides for the use of a computer 4. This configuration is suited for rapidly carrying out the various total body fat, lean body mass and/or total body water determinations for a large number of individuals and to automate the updating of the history. However, all of the calculations described above with reference to the various modules of the computer may just as well be carried out directly by the operator. This situation is encountered in particular when the total body fat, lean body mass and total water determinations have to be performed in succession at different locations.

Thus, the invention lends itself particularly well to the case in which these determinations have to be performed in a portable manner.

What is claimed is:

1. A method of determining the total body fat of a person, comprising:

measuring, with an ultrasonic probe, a subcutaneous fat thickness at four points on the person's body, located in the right anterior part of the left mid-thigh, in the left anterior part of the right mid-thigh, in the right dorsal part of the body at navel level and in the left dorsal part of the body at navel level, respectively; and determining, with a computer, a first estimate of the person's total body fat as a function of only the following parameters:

the subcutaneous fat thickness measurements at said four points;

the body mass index of the person, defined as the ratio of the person's weight in kilograms to the square of the person's height in meters;

the waist perimeter passing through the navel of the person;

the sex of the person; and the average of the left and right leg perimeters passing at mid-thigh;

wherein the first estimate of the person's total body fat is obtained using the equation below:

$FAT = a \times BMI + b \times T_{nav,l} + c \times T_{nav,r} + d \times WP + e \times T_{thigh,r} + f \times T_{thigh,l} + g \times AP_{thigh} + \text{constant}$, where FAT is the first estimate of the total body fat in kg, BMI is the ratio of the person's weight in kg to the square of his height in m, WP is the waist perimeter passing through the navel, $AP_{thigh}$ is the average of the left and right leg perimeters passing at mid-thigh, $T_{nav,l}$, $T_{nav,r}$, $T_{thigh,r}$ and $T_{thigh,l}$, are the fat thicknesses measured in the left dorsal part at navel level, in the right dorsal part at navel level, in the right anterior part of the left mid-thigh and in the left anterior part of the right mid-thigh, in mm, respectively, and where a=0.959, b=0.119, c=−0.044, d=0.13, e=0.586, f=−0.329, g=0.061 and constant=−23.88, when the person is of the female sex; and a=0.733, b=−0.053, c=0.102, d=0.27, e=0.155, f=−0.106, g=0.015 and constant=−31.21 when the person is of the male sex.

2. The method as claimed in claim 1 wherein the first estimate of the person's total body fat is a linear function of the subcutaneous fat thickness measurements at said four points.

3. The method as claimed in claim 1, further comprising:
comparing the first estimate of the person's total body fat with a threshold value defined by the sex of the person; and
determining a second estimate of the person's total body fat as a function of the results of said comparison and of the subcutaneous fat thickness measurements at said four points.

4. The method as claimed in claim 3, wherein the second estimate of the person's total body fat is also a function of at least values representative of the perimeter around the waist passing through the navel, the perimeter around the leg passing through mid-thigh, the body mass index, defined as the ratio of the person's weight to the square of his height, and the sex of the person.

5. The method as claimed in claim 3, wherein the second estimate of the person's total body fat is obtained using a linear function of the subcutaneous fat thickness measurements at said four points.

6. The method as claimed in claim 3, wherein the second estimate of the person's total body fat is obtained using the equation below:

$FAT = a \times BMI + b \times T_{nav,l} + c \times T_{nav,r} + d \times WP + e \times T_{thigh,r} + f \times T_{thigh,l} + g \times AP_{thigh} + constant$, when the person is of the female sex, where FAT is the first estimate of the total body fat in kg, BMI is the ratio of the person's weight in kg to the square of his height in m, WP Is the length of the waist perimeter passing through the navel, $AP_{thigh}$ is the average of the length of the left and right leg perimeters passing at mid-thigh, $T_{nav,l}$, $T_{nav,r}$, $T_{thigh,r}$, and $T_{thigh,l}$ are the fat thickness measured in the left dorsal part of the body at the navel level, in the right dorsal part of the body at the navel level, in the right anterior part of the left mid-thigh and in the left anterior part of the right mid-thigh, in mm, respectively, and where a=0.947, b=0.079, c=0.0067, d=0.103, e=−0.303, f=0.379, g=0.072 and constant=−20.58 if the first estimate is below the predefined threshold of 42 kg, and a=−0.743, b=−1.73, c=1.10, d=1.677, e=−3.35, f=2.62, g=−4.95 and constant=242.53 if the first estimate is equal to or greater than the predefined threshold of 42 kg, and using the following equation when the person is of the male sex:

$FAT = a \times BMI + b \times T_{nav,l} + c \times T_{nav,r} + d \times WP + e \times T_{thigh,r} + f \times T_{thigh,l} + g \times AP_{thigh} + h \times T_{thigh,av} + i \times T_{nav,av} + constant$ where $T_{thigh,av}$ is the average fat thickness at mid-thigh and at $T_{nav,av}$ is the average dorsal fat thickness a navel level, and where a=0.221, b=0.032, c=0.06, d=0.253, e=0.078, f=−0.0128, g=0.073, h=−0.048, i=−0.028 and constant=−21.2 if the first estimate is below the predefined threshold of 22 kg and a=1.31, b=−2.69, c=−1.76, d=−0.175, e=10.33, f=8.91, g=−0.123, h=−18.97, i=4.72 and constant=−10.88 if the first estimate is equal to or greater than the predefined threshold of 22 kg.

7. The method as claimed in claim 1, wherein the subcutaneous fat thickness values are measured using an ultrasound device.

8. The method as claimed in claim 1, further comprising: from the body fat determined, a value of the lean body mass and a value of the total body water present in the person's body are determined.

9. The method as claimed in claim 8, in which the value of the lean body mass is equal to the person's weight from which a determined fat value is subtracted and the total body water value is equal to: $W_{body} = 0.692 \times LBM + 1.572$, where $W_{body}$ is the total body water in liters and LBM is the lean body mass in kilograms.

10. A system for determining a person's total body fat, comprising:
an ultrasonic probe configured to measure a subcutaneous fat thickness at four points on the person's body, located in the right anterior part of the left mid-thigh, in the left anterior part of the right mid-thigh, in the right dorsal part of the body at navel level and in the left dorsal part at navel level, respectively; and
a computer configured to determining a first estimate of the person's total body fat as a function of:
the subcutaneous fat thickness measurements at said four points,
the body mass index of the person, defined as the ratio of the person's weight in kilograms to the square of the person's height in meters;
the waist perimeter passing through the navel of the person;
the sex of the person; and
the average of the left and right leg perimeters passing at mid-thigh;
wherein the first estimate of the person's total body fat is obtained using the equation below:

$FAT = a \times BMI + b \times T_{nav,l} + c \times T_{nav,r} + d \times WP + e \times T_{thigh,r} + f \times T_{thigh,l} + g \times AP_{thigh} + constant$, where FAT is the first estimate of the total body fat in kg, BMI is the ratio of the person's weight in kg to the square of his height in m, WP is the waist perimeter passing through the navel, $AP_{thigh}$ is the average of the left and right leg perimeters passing at mid-thigh, $T_{nav,l}$, $T_{nav,r}$, $T_{thigh,r}$ and $T_{thigh,l}$, are the fat thicknesses measured in the left dorsal part at navel level, in the right dorsal part at navel level, in the right anterior part of the left mid-thigh and in the left anterior part of the right mid-thigh, in mm, respectively, and where a=0.959, b=0.119, c=−0.044, d=0.13, e=0.586, f=−0.329, g=0.061 and constant=−23.88, when the person is of the female sex; and a=0.733, b=−0.053, c=0.102, d=0.27, e=0.155, f=−0.106, g=0.015 and constant=−31.21 when the person is of the male sex.

11. A system for determining a person's body composition, comprising:
an ultrasonic probe configured to measure a subcutaneous fat thickness at four points on the person's body, located in the right anterior part of the left mid-thigh, in the left anterior part of the right mid-thigh, in the right dorsal part of the body at navel level and in the left dorsal part of the body at navel level, respectively; and
a computer configured to determine a first estimate of the person's total body fat as a function of:
the subcutaneous fat thickness measurements at said four points;
the body mass index of the person, defined as the ratio of the person's weight in kilograms to the person's height in meters;
the waist perimeter passing through the navel of the person;
the sex of the person; and
the average of the left and right leg perimeters passing at mid-thigh;
wherein the first estimate of the person's total body fat is obtained using the equation below:

$FAT = a \times BMI + b \times T_{nav,l} + c \times T_{nav,r} + d \times WP + e \times T_{thigh,r} + f \times T_{thigh,l} + g \times AP_{thigh} + constant$, where FAT is the first estimate of the total body fat in kg, BMI is the ratio of the person's weight in kg to the square of his height in m, WP is the waist perimeter passing through the navel, $AP_{thigh}$ is the average of the left and right leg perimeters passing at mid-thigh, $T_{nav,l}$, $T_{nav,r}$, $T_{thigh,r}$ and $T_{thigh,l}$, are the fat thicknesses measured in the left dorsal part at navel level, in the right dorsal part at navel level, in the right anterior part of the left mid-thigh and in the left anterior part of the right mid-thigh, in mm, respectively, and where a=0.959, b=0.119, c=−0.044, d=0.13, e=0.586, f=−0.329, g=0.061 and constant=−23.88, when the person is of the female sex; and a=0.733, b=−0.053, c=0.102, d=0.27, e=0.155, f=−0.106, g=0.015 and constant=−31.21 when the person is of the male sex; and the computer being further configured to determine, from the determined fat value, a value of the lean body mass and a value of the total body water present in the person's body.

* * * * *